United States Patent [19]

Sorensen

[11] Patent Number: 5,685,170
[45] Date of Patent: Nov. 11, 1997

[54] PROPANE RECOVERY PROCESS

[75] Inventor: James N. Sorensen, Calgary, Canada

[73] Assignee: McDermott Engineers & Constructors (Canada) Ltd., Calgary, Canada

[21] Appl. No.: 727,894

[22] Filed: Oct. 9, 1996

Related U.S. Application Data

[60] Provisional application No. 60/007,225, Nov. 3, 1995.

[51] Int. Cl.[6] ............................................. F25J 3/00
[52] U.S. Cl. ......................... 62/625; 62/632; 62/635
[58] Field of Search ............................. 62/625, 632, 635

[56] References Cited

U.S. PATENT DOCUMENTS

| | | | |
|---|---|---|---|
| 4,157,904 | 6/1979 | Campbell et al. | 62/27 |
| 4,278,457 | 7/1981 | Campbell et al. | 62/24 |
| 4,473,385 | 9/1984 | Fabian et al. | 62/625 |
| 4,559,070 | 12/1985 | Sweet | 62/625 |
| 4,657,571 | 4/1987 | Gazzi | 62/625 |
| 4,680,042 | 7/1987 | Mehra | 62/17 |
| 4,687,499 | 8/1987 | Aghili | 62/24 |
| 4,695,303 | 9/1987 | Montgomery, IV et al. | 62/24 |
| 4,695,672 | 9/1987 | Bunting | 62/625 |
| 4,696,688 | 9/1987 | Mehra | 62/17 |
| 4,698,081 | 10/1987 | Aghili | 62/24 |
| 4,832,718 | 5/1989 | Mehra | 62/17 |
| 4,851,020 | 7/1989 | Montgomery IV | 62/24 |
| 4,854,955 | 8/1989 | Campbell et al. | 62/24 |
| 4,869,740 | 9/1989 | Campbell et al. | 62/24 |
| 4,883,515 | 11/1989 | Mehra et al. | 62/17 |
| 4,889,545 | 12/1989 | Campbell et al. | 62/24 |
| 5,275,005 | 1/1994 | Campbell et al. | 62/24 |
| 5,325,673 | 7/1994 | Durr et al. | 62/23 |

FOREIGN PATENT DOCUMENTS

| | | | |
|---|---|---|---|
| 1048397 | 2/1979 | Canada | 162/19 |
| 1073804 | 3/1980 | Canada | 162/17 |

*Primary Examiner*—Ronald C. Capossela
*Attorney, Agent, or Firm*—Daniel S. Kalka; Robert J. Edwards

[57] ABSTRACT

Increased recovery of propane, butane and other heavier components found in a natural gas stream is achieved by installing an absorber upstream from an expander and a separator. The separator is downstream from the expander and returns the liquid stream generated by the separator back to the absorber. Additionally, the recovery of propane, butane and other heavier components is enhanced by combining the upper gas stream from a distillation column with the upper gas stream from the absorber prior to injecting this combination into the separator. The upper gas stream removed from the separator is then subsequently processed for the recovery of a predominately methane and ethane gas stream while the bottom liquid stream from the absorber is subsequently distilled for the generation of a stream consisting predominately of propane, butane and other heavy hydrocarbon components. Alternate embodiments include an additional reflux separator in the system, or substitution of an additional absorber for the separator.

22 Claims, 3 Drawing Sheets

PROPANE RECOVERY PROCESS

This application is based on provisional application Ser. No. 60/007,225 filed on Nov. 3, 1995.

BACKGROUND OF THE INVENTION

1. Field of the Invention

This invention pertains to a system and a process for recovering propane, butane and heavier hydrocarbon components from natural gas thereby also generating a gas stream consisting primarily of methane and ethane.

2. Description of the Related Art

Many methods currently exist for processing hydrocarbon gas. Some typical examples of isolating and extracting desired components of the hydrocarbon gas are disclosed in U.S. Pat. Nos. 4,680,042, 4,696,688, 4,832,718 and 4,883,515 to Mehra and others. These patents generally disclose the removal of a methane rich gas product from an inlet gas stream while also generating a product stream containing ethane, propane, butane and other heavier hydrocarbon components. The isolation of methane is accomplished by returning a lean solvent from a hydrocarbon product column and injecting same near the top of an extractor-stripper (ES) column. This lean solvent is used to absorb the heavier hydrocarbon components of the raw gas supplied to the extractor-stripper column. In this fashion, the methane rich gas product is removed from the top of the extractor-stripper column.

Additional methods of processing hydrocarbon gas are disclosed in U.S. Pat. Nos. 4,854,955, 4,869,740, 4,889,545, and 5,275,005 to Campbell et al. These patents all disclose the step of expanding a vapor received from a separator prior to delivering same to a distillation column.

U.S. Pat. Nos. 4,507,133 and 4,617,039 each disclose a step of expanding a vapor received from a separator and contacting same in an absorber with absorbed components delivered to a distillation column.

U.S. Pat. No. 5,325,673 to Durr et al. discloses a method of pre-treating a natural gas stream using a single scrub column in order to remove freezable $C_{5+}$ components. This method consists of feeding a natural gas stream to a feed point on a scrub column operated substantially as an absorption column wherein the heavy components are absorbed from the feed gas using a liquid reflux that is essentially free of such $C_{5+}$ components. Durr et al. also teaches that the reflux stream can be overhead vapor condensate having a temperature of about $-40°$ C., or methane-rich liquified natural gas (LNG) or a combination of LNG and vapor condensate.

While a variety of different processes are disclosed, none teach the use of a separator located downstream of a turbo-expander from which a liquid stream is being returned to an absorber which is located upstream of the turbo-expander. It is thus an object of this invention to not only provide for such a process, but to also provide a means of removing freezable hydrocarbon components from natural gas prior to liquefaction in order to facilitate its transportation. A further object of this invention is to generally replace the typically used separator with an absorber so that as incoming gas flows upward therethrough, downward flowing hydrocarbon liquid selectively absorbs more of the propane and heavier components in the incoming gas and less of the ethane and lighter components. A further object of this invention is to pump cryogenic hydrocarbon liquid from a downstream separator that is coupled to the expander outlet of the compressor/expander. This pump delivers the hydrocarbon liquid either directly or through a heat exchanger and then recycles it back to the upstream absorber. Yet another object of this invention is to deliver the gas leaving the upper region of the distillation column to a heat exchanger. In one variation of the process, this heat exchanger cools and partially condenses said gas which then flows to and joins the feed to the separator that is coupled to the expander outlet. In another variation, a portion of the process feed gas is chilled using the gas from the overhead of the distillation column (which may or may not be mixed with the overhead of the separator which is downstream of the expander), this portion of the chilled feed gas is then used to cool the overhead gas stream from the distillation tower and the heat so acquired is then used to reboil the bottom of the absorber.

SUMMARY OF THE INVENTION

An improvement is described to a process for recovering propane and other heavier components from a natural gas stream. This process incorporates the step of locating a separator downstream of a turbo-expander and removing a liquid stream from the separator. This liquid stream removed from the separator is then returned and injected into an upper region of the upstream absorber. In the absorber, this liquid stream absorbs propane and heavier hydrocarbon compounds from the natural gas stream fed into the absorber. A methane and ethane rich gas stream is then removed from the downstream separator while a stream rich in propane, butane, and other heavy hydrocarbon components of the natural gas stream is removed from the bottom of the absorber and routed to the distillation column for separation of the light and heavy components.

DESCRIPTION OF THE PREFERRED EMBODIMENT

Figure 1:
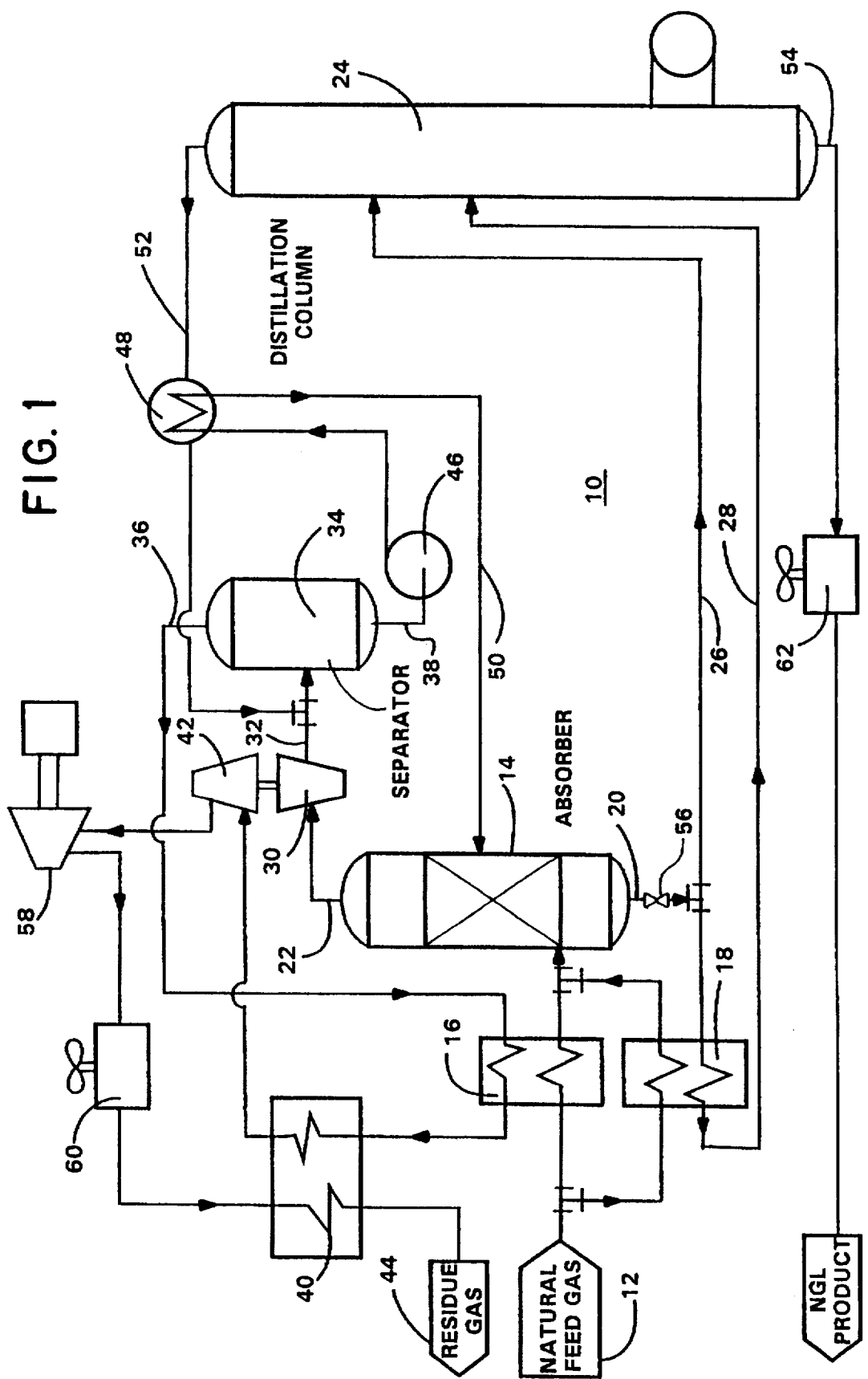
FIG. 1 is a schematic diagram of the system and process (10) disclosed herein. While parts of this schematic are well known in the art, the interconnections and arrangement of the absorber, expander, separator and distillation column comprise the core of this invention.

Referring to FIG. 1, there is shown a schematic of the system and process (10) which comprises one embodiment of the present invention. Natural gas (12) feed is injected into a lower region of absorber (14) after being chilled in heat exchangers (16) and (18).

As the chilled and partially condensed feed gas (12) passes through absorber (14), the gaseous portion thereof flows upward through a packed section or other contacting device such as a trayed section, while the liquid portion thereof flows downward. Discharged from absorber (14) is bottom liquid stream (20) and upper gas stream (22).

As indicated, a portion of bottom liquid stream (20) flows directly to an upper region of distillation column or deethanizer (24) via line (26) and a portion of this bottom liquid stream (20) from absorber (14) is warmed in heat exchanger (18) and then delivered to a more central region of distillation column or deethanizer (24) via line (28). The split may vary from all to line (26) to all line (28).

Upper gas stream (22) exiting absorber (14) is then delivered to expander (30) of a compressor/expander. The ensuing expansion of gas stream (22) liquifies a portion of it with the resultant liquid-gas stream (32) exiting expander (30) and being delivered directly to separator (34).

It is within separator (34) that the incoming liquid-gas stream (32) is separated into upper gas stream (36) and lower liquid stream (38). In this embodiment, upper gas stream (36) is then cross-exchanged with incoming natural feed gas (12) in heat exchanger (16). The effect is to chill stream (12) while warming stream (36). Subsequent heat exchange or warming of gas stream (36) in heat exchanger (40) is achieved after which gas stream (36) from separator (34) enters the compressor side (42) of the compressor/expander. The now pressurized gas stream may then be further compressed and cooled, if so desired, before the resulting residue gas (44), consisting primarily of methane and ethane, is delivered elsewhere.

Referring back to separator (34), and more specifically to the lower liquid stream (38), this stream is pumped via pump (46) to heat exchanger (48) for warming before being delivered or recycled back to absorber (14) via line (50). In a typical process, this bottom liquid stream (38) would be sent directly to distillation column (24); however, in process (10), such liquid stream (38) is instead warmed and partially vaporized in heat exchanger (48) and returned to absorber (14). This warmed and partially vaporized liquid stream (50), separates from the vapor at the top of absorber (14), and then flows downward in absorber (14). During such downward flow, the liquid from stream (50) absorbs more of the propane and heavier components in the gas entering the absorber and less of the ethane and lighter components which remain in their gaseous state for discharge via gas stream (22).

Referring now to distillation column or deethanizer (24), upper gas stream (52) is discharged therefrom and sent to heat exchanger (48) for cooling via cross-exchange with cold liquid stream (38) from separator (34). This now cooled gas stream (52) is then delivered and mixed with liquid/gas stream (32) before this stream (32) enters separator (34). This recycle of gas stream (52) from distillation column (24) aids or improves the recovery of hydrocarbons in process (10). To maximize the recovery of propane and heavier components, the duty of heat exchanger (48) is maximized consistent with economical temperature approaches. Bottoms product liquid stream (54) from distillation column (24), which consists primarily of propane, and other heavier components, is also cooled as shown and delivered elsewhere for further processing and/or use.

Thus, some of the pertinent features of this process (10) include pump (46) which pumps cryogenic hydrocarbon liquid (38) from separator (34) that is coupled to the outlet of expander (30). This liquid stream (38) is delivered to absorber (14), located upstream of expander (30), but generally after being warmed in heat exchanger (48). By warming liquid stream (38) in heat exchanger (48), a hydrocarbon two-phase stream is generated that travels through line (50) before being injected at or near the top of absorber (14). The vapor portion of two-phase stream (50) that is injected into absorber (14) adds to the vapor leaving absorber (14) in upper gas stream (22). This upper gas stream (22), as explained earlier, then enters expander side (30) of an expander/compressor. Such extra vapor now passing through expander (30) increases the refrigeration effect of process (10) since additional work is done by the increased quantity of expanding gas. Furthermore, more power is now supplied to compressor side (42) of the expander/ compressor which is used to compress methane and ethane rich gas stream (36).

Absorber (14) may comprise any number of theoretical stages. It may consist of phase separation of stream (12) followed by one or more contacting stages or it may be just a separator in which case stream (50) is optimally combined with stream (12) before entering the separator.

Bottom liquids product (20) from absorber (14) is, as indicated, flashed through valve (56) thereby resulting in a two-phase stream passing through lines (26) and/or (28). Line (26) is used as a reflux to deethanizer (24) while line (28) is delivered to heat exchanger (18) for warming prior to entering distillation column (24). Depending on the two-phase flow characteristics it may be preferable that stream (20) be split first and then let down in pressure via separate control valves passing streams (26) and (28).

It is anticipated that the recovery of propane by this process will generally exceed 90% while the recovery of butane and heavier ends will be about 100%, this recovery being in the NGL product or bottoms product (54).

A typical example of process (10) would be as follows (with the specified temperatures (°F.) and pressures (psia) only being approximations). Natural gas feed (12) enters process (10) at a temperature of 80° F. and a pressure of 580 psia. After appropriate portions of gas pass through heat exchanger (16) and (18), the resultant temperature and pressure of feed gas (12) are about −93° F. and 575 psia. It is at these values that gas stream (12) enters absorber (14). Bottom liquid product (20) and upper gas stream (22) exiting absorber (14) are also at about the same temperature and pressure as incoming gas (12) however their compositions are significantly different. Upper gas stream (22) remains methane and ethane rich, but its concentrations of propane, butane and other heavier components are significantly reduced. In contrast, bottom liquid product (20) still contains some relatively small concentrations of methane and ethane, but it also contains all or nearly all of the propane, butane and heavier components originally found in natural feed gas stream (12).

Upper gas stream (22) leaving absorber (14) is at about −90° F. and at a pressure of about 574 psia; however, after passing through expander (30), the resulting liquid/gas stream (32) is at a temperature of about −116° F. and a pressure of 384 psia. Upon mixing with gas stream (52) from deethanizer (24), the resulting stream entering separator (34) is at a temperature of about −113° F. and a pressure of about 382 psia. The combined streams (i.e. (32) and (52)) remain very methane and ethane rich while containing relatively low, if insignificant, quantities of propane, butane and the like.

Exiting separator (34) are methane and ethane rich gas stream (36) and propane rich liquid stream (38) at similar temperatures and pressures. Methane and ethane rich gas stream (36) is then used to cool incoming natural feed gas (12) via heat exchanger (16). After such cross-exchange, gas stream (36) is at a temperature of about 71° F. and 377 psia. Subsequent warming in heat exchanger (40) generates a stream at about 101° F. and 372 psia. It is at this temperature and pressure that gas stream (36) enters compressor (42). Leaving compressor (42), stream (36) continues to contain predominantly methane and ethane and only small to insignificant quantities of propane, butane and the like at a temperature of about 119° F. and at a pressure of 414 psia.

Further compression in compressor (58) does not affect its composition, but the temperature of stream (36) increases to about 189° F. and its pressure to 622 psia. Subsequent cooling, such as via air cooler (60), drops this temperature to about 109° F. while its pressure remains about the same. The temperature of this stream (36) is generally further reduced in heat exchanger (40) by cross-exchange with itself prior to being compressed in compressor (42) and/or (58). The resulting residue gas stream (44), which consists predominantly of methane and ethane and only token quantities of propane or other heavier hydrocarbons, is delivered from process (10) at a temperature of about 80° F. and a pressure of 613 psia.

Referring now to liquid stream (38) from separator (34), this liquid stream (38) also contains some methane and ethane, but of lesser concentrations than that found in gas stream (36). However, the quantity of propane, butane and other heavier components are much greater in liquid stream (38) than in gas stream (36). This propane and butane rich stream (38) from separator (34) is delivered to pump (46) where its pressure is increased to about 587 psia with a temperature of about −110° F. Subsequent cross-exchange of this stream (38) in heat exchanger (48) results in its temperature being increased to about −46° F. with its pressure remaining about the same.

It is at this stage that this liquid propane and butane rich stream (50) is returned to an upper region of absorber (14) with the down-flowing liquid portion of this stream absorbing some of the heavier components of the natural gas feed stream (12) into the liquid, thereby increasing its concentration of such heavier components. The resulting bottom liquid stream (20) is at a temperature of about −94° F. and a pressure of about 575 psia. However, the bottom liquid stream (20) now contains even greater concentrations of propane and heavier components. In fact, it is likely that bottoms liquid stream (20) contains greater concentrations of such components than found in the incoming feed gas stream (12) while the concentrations of methane and ethane in liquid stream (20) are significantly less than that found in the liquid portion of natural gas feed stream (12).

Upon being flashed across valve (56), bottom liquid stream (20) is at a temperature of about −113° F. and a pressure of about 401 psia. A portion of this stream is sent via line (26) for use as reflux in deethanizer column (24). The remaining portion is sent via line (28) first to heat exchanger (18) for cross-exchange with incoming feed gas (12). Afterwards, this now warmed portion is also sent to deethanizer (24), however its temperature is about 44° F.

At deethanizer (24), as its name implies, the ethane and lighter components are stripped from the incoming streams (26) and (28) and discharged via upper gas stream (52). The propane and heavier components are discharged via bottoms product (54). This bottoms product (54) contains none to insignificant quantities of ethane and methane therein. Likewise, upper methane and ethane rich gas stream (52) contains small to insignificant quantities of propane, butane and the like therein.

Upper methane and ethane rich gas stream (52) leaves deethanizer (24) at a temperature of about −37° F. and at a pressure of about 387 psia. After being cooled by cross-exchange with liquid stream (38) from separator (34) in heat exchanger or deethanizer overhead condenser (48), its temperature is reduced to about −96° F. Upon such cooling, this methane and ethane rich stream (52) is combined with liquid-gas stream (32) for delivery to separator (34) so that separation of the lighter components (methane and ethane) from the heavier components (propane, butane, pentane, hexane and the like) are accomplished as previously described.

Propane and butane rich bottoms product (54) leaves deethanizer (24) at a temperature of about 192° F. and a pressure of about 392 psi. This bottoms product stream (54) is cooled in air cooler (62) to a temperature of about 109° F. Afterwards, this propane and butane rich stream is sent elsewhere for processing.

Figure 2:
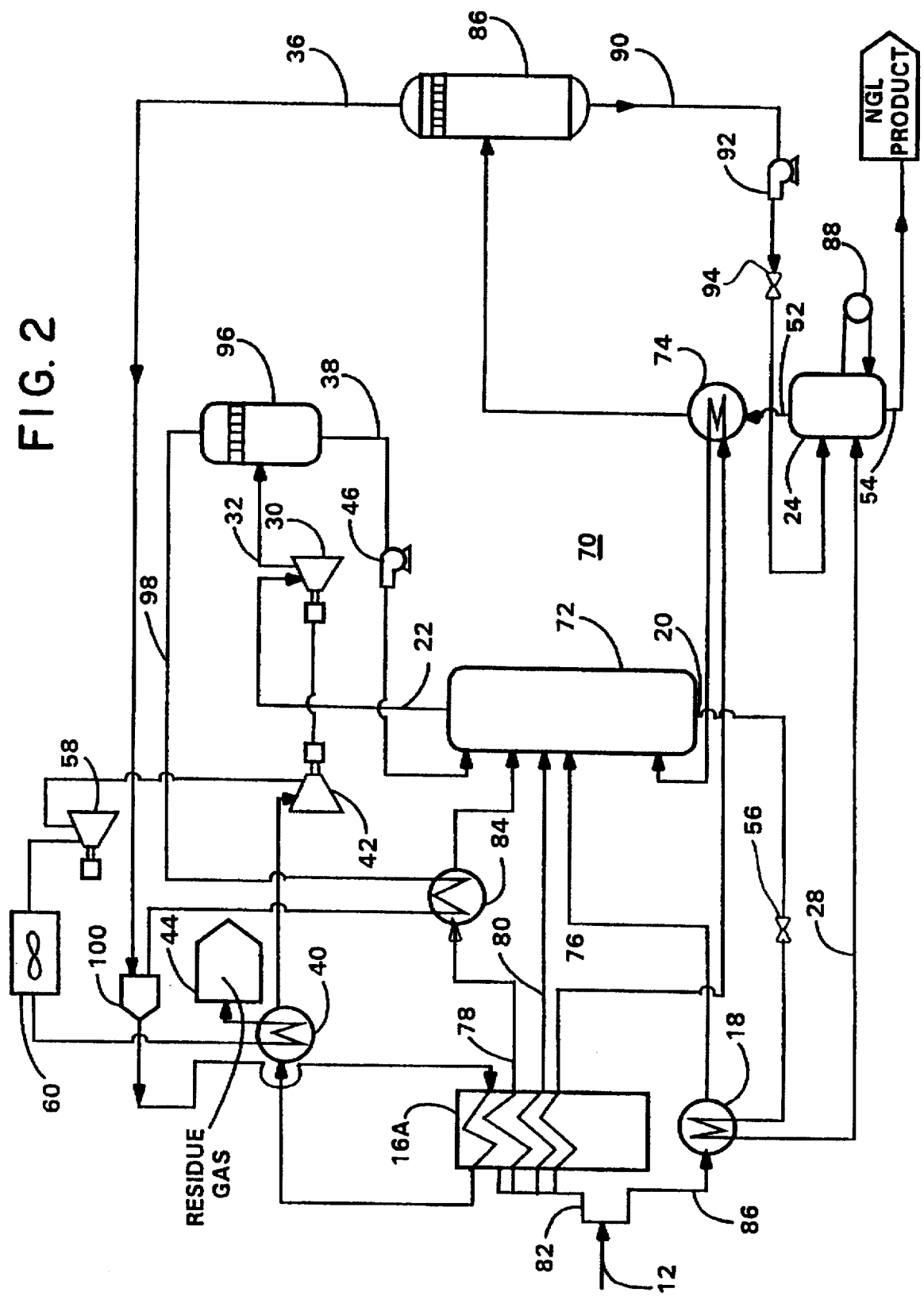
FIG. 2 is a schematic diagram of an alternate system and process (70).

Referring now to FIG. 2, there is shown a schematic diagram of an alternate system and process according to the present invention. Like numerals designate like or similar features throughout the several views. The alternate system and process (70) is quite similar to process (10) shown in FIG. 1. The advantages of the alternate process (70) are greater flexibility in design and greater propane recovery for the same compression horsepower. The recovery of propane will be generally greater than 95% using process (70). In this process, a reboiled absorber (72) is used instead of absorber (14). Advantageously, a reboiler (74) strips out a large portion of the methane and ethane that would otherwise enter the deethanizer (24) so that the deethanizer does not have to fractionate so hard. The reboiler (74) in this design also serves as an overhead reflux condenser for the deethanizer. The reboiler (74) provides stripping vapor in stream (76) to the bottom of the absorber (72).

Another feature of this design is a cold feed stream (78) to the absorber (72) which is developed by cooling it by heat exchange with expander (30) outlet vapors in heat exchanger (84). This alternate process (70) is only slightly more complex than process (10) with one additional exchanger (84), one additional vessel (86), and one additional pump (92).

As seen in FIG. 2, natural gas feed (12) is split into two portions (82) and (86). Stream (86) is cooled in heat exchanger (18). Stream (82) is further split into streams (76), (78) and (80) which are cooled in heat exchanger (16A). Portion (78) is further cooled in heat exchanger (84) as described earlier and injected into a mid-region of absorber (72). Portion (80) is directly introduced into the absorber (72) in a slightly lower stage or tray. The third portion (76) passes through reboiler (74) where it is used to cool and partially condense deethanizer (24) outlet vapor stream (52), and then stream (76) is introduced into the lower region of absorber (72).

The cooled feed stream (86) is also directly introduced in the lower region of absorber (72) at a temperature less than the third portion (76).

Bottom liquid stream (20) flows through valve (56) to lower the pressure and temperature and is warmed in heat exchanger (18) before being delivered to a central region of the distillation column or deethanizer (24) via line (28). While deethanizer (24) is shown smaller in size in FIGS. 2 and 3, it is understood that it is identical in structure and function to that shown in FIG. 1 as the like numeral (24) indicates.

In deethanizer (24), upper gas stream (52) which is methane and ethane rich is discharged and passed through reboiler (74). Reboiler (74) causes a large portion of the methane and ethane to be stripped from the feed to absorber (72) so that deethanizer (24) does not have to fractionate so hard. Reboiler (74) also serves as an overhead reflux condenser for deethanizer (24). The upper gas stream (52) passes through reboiler (74) and enters reflux separator (86). Bottom product liquid stream (54) from deethanizer (24), which consists primarily of propane, butane, pentane and other heavy hydrocarbons, may be cooled with optional cooler (62) (as shown in FIG. 1).

Referring back to reflux separator (86), upper gas stream (52) is separated into a methane and ethane rich upper gas stream (36) which has a flow path similar to that described for FIG. 1 and a lower propane rich liquid stream with some small concentrations of methane and ethane (90). The lower liquid stream (90) is sent via pump (92) through level control valve (94) back into the upper region of deethanizer (24) for fractionation.

Referring back to the absorber (72), upper gas stream (22) remains methane and ethane rich with concentrations of propane, butane and other heavier components significantly reduced. Stream (22) is discharged from absorber (72) and passes through an expansion means like turbo-expander (30) of compressor (42)/expander (30) which are preferably serially connected. The liquid/gas stream (32) exiting expander (30) enters reflux separator (96) where liquid/gas stream (32) is separated into an upper methane and ethane rich gas stream (98) and a lower liquid propane rich stream (38). Lower liquid stream (38) is pumped via pump (46) to the upper region of absorber (72). The upper gas stream (98) passes through heat exchanger (84) to cool feed stream (78) and then is combined through a tee (100) with upper gas stream (36) from reflux separator (86).

A typical example of process (70) would be as follows with the specified temperatures and pressures representing approximations of a simulated model. Natural gas feed (12) enters process (70) at a temperature of about 86° F. at a pressure of about 612 psia. The upper portion (82) is split into streams (76), (78) and (80) which are cooled to about −71° F. The lower portion (86) is cooled to about −40° F. with a pressure of about 609 psia. Stream (78) is further cooled to about −112° F. with a pressure of about 606 psia. Stream (80) flows directly to absorber (72). Streams (76) and (78) are cooled respectively to about −70° F. and −112° F. and flow to absorber (72). Bottom liquid product (20) exits absorber (72) at a temperature of about −38° F. and a pressure of about 606 psia. Upper gas stream (22) exits absorber (72) at a temperature of about −99° F. and about 605 psia. After going through expander (30), stream (32) is at a temperature of about −122° F. and a pressure of about 413 psia. Gas stream (98) is at a temperature of about −122° F. and 413 psia exiting reflux separator (96). After passing heat exchanger (84), the temperature of stream (98) is warmed to about −88° F. and is about 408 psia. Stream (98) is combined with upper gas stream (36) from reflux separator (86). The combined stream is at a temperature of about −87° F. and a pressure of about 408 psia. The combined stream is warmed in heat exchanger (16A) to a temperature of about 78° F. with a pressure of about 403 psia. Next, the stream is warmed in heat exchanger (40) to a temperature of about 86° F. and a pressure of about 628 psia whereafter it is compressed in compressors (42) and (48), cooled in air cooler (60) and heat exchanger (40), and exits the process as a residue gas stream (44) which consists predominantly of methane and ethane. Lower liquids stream (20) is warmed in heat exchanger (18), and enters the deethanizer (24) at a temperature of about −66° F. and a pressure of about 416 psia.

The upper gas stream (52) exiting deethanizer (24) is at a temperature of about 12° F. and a pressure of about 413 psia. The lower liquid stream which is the NGL product stream containing the propane, butane and like fractions is at a temperature of about 195° F. and a pressure of about 416 psia. Reflux separator (86) receives the upper stream (52) at a temperature of about −34° F. and a pressure of about 408 psia. This stream is separated into an upper stream (36) and a lower liquid stream (90) at about the same pressure and temperatures.

Figure 3:
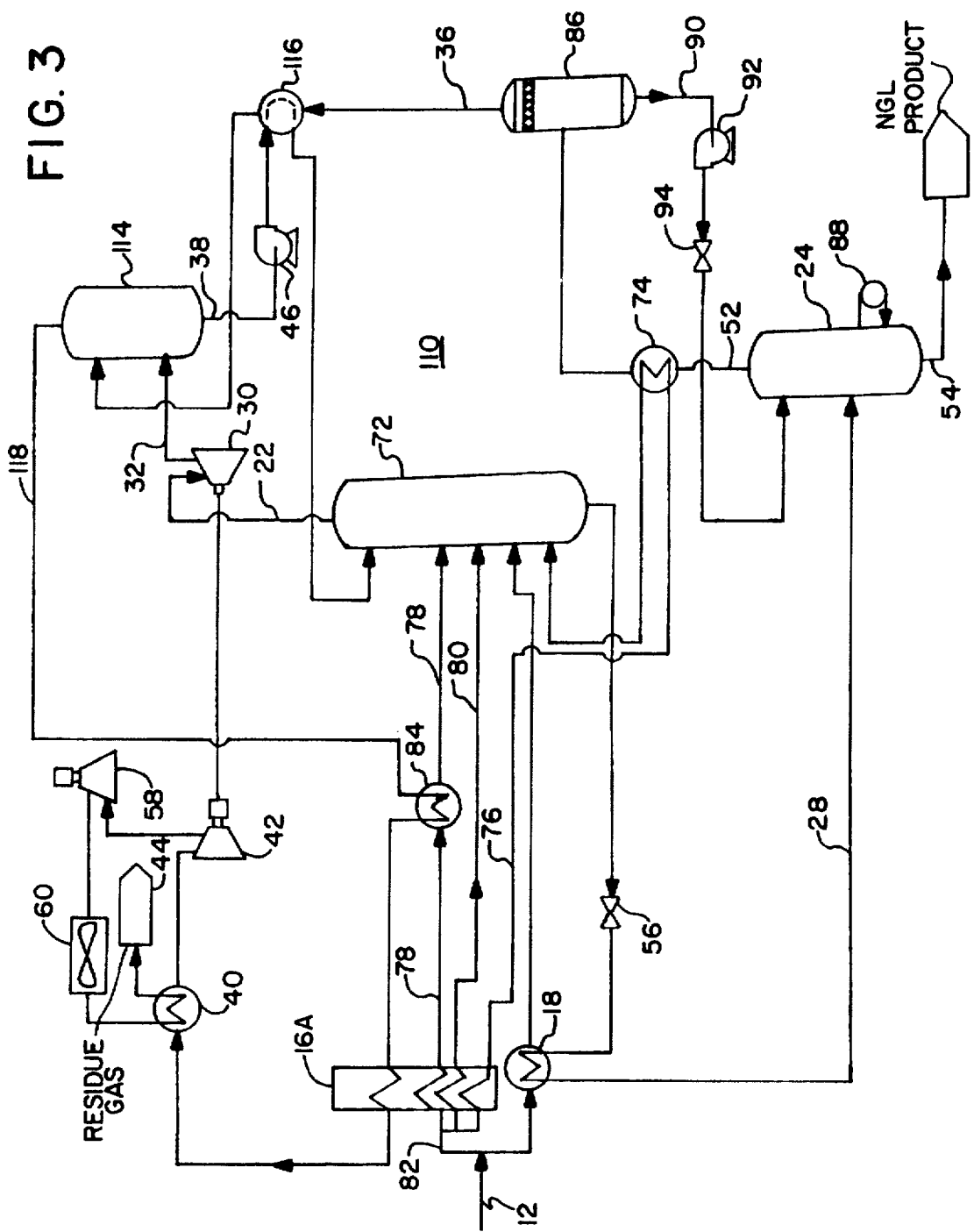
FIG. 3 is yet another schematic diagram of a further alternate system and process (110).

Referring next to FIG. 3, there is shown still another embodiment of the present invention where like numerals designate like or similar features. The system and process (110) shown in FIG. 3 obtains a very high propane recovery of about 99.2%. FIG. 3 is similar to FIGS. 1 and 2 except that reflux separator (96) has been replaced with an additional absorber (114). Absorber (114) receives liquid/gas stream (32) from expander (30) in the lower region of the absorber. Absorber (114) also receives upper gas stream (36) from reflux separator (86). Upper gas stream (36) passes through heat exchanger (116) where it is cooled and partially condensed prior to entering the upper region of absorber (114). Absorber (114) operates in a manner similar to absorbers (14) and (72), and may contain either packing, trays, or other contacting means. The upper gas stream (118) from absorber (114) is warmed in heat exchangers (84) and (16A) where it first cools feed stream (78), and then (76), (78), and (80) respectively. It then flows in a similar path to that described with reference to FIG. 2. The temperature and pressures provided for FIG. 2 are approximately the same for FIG. 3. The absorber (114) receives liquid-gas stream (32) at a temperature of about −120° F. as compared with −122° F. for the liquid/gas stream (32) entering reflux separator (96) in FIG. 2.

The absorbers (14), (72), (114) may be any contacting device operating in the manner described. Similarly, other modifications including addition or substitution of equivalent structures may be made to the system. Referring to FIG. 1, one such modification could be to insert a separator in which streams (50) and (12) combine upstream of absorber (14). A dephlagmator (refluxing heat exchanger) could be installed above the separator. Stream (36) could cool the dephlagmator.

Likewise, expander (30) may be any expansion means such as a turbo-expander, two turbo-expanders operating in series, or a Joule-Thompson expansion valve.

Also, the number of stages or trays in absorbers (72, 114) depends on the inlet composition of the feed gas and other factors including process economics.

While specific embodiments of the invention have been shown and described in detail to illustrate the application and principles of the invention, certain modifications and improvements will occur to those skilled in the art upon reading the foregoing description. It is thus understood that such modifications and improvements have been excluded herein for the sake of conciseness and readability but are properly within the scope of the following claims.

I claim:

1. In a propane recovery process, the method comprising the steps of:

providing an absorber for receiving a natural gas stream and passing it upwardly therethrough, said absorber separating the natural gas stream into an upper gas stream and a bottom liquid stream;

providing an expander downstream from said absorber for receiving and expanding the upper gas stream from said absorber;

locating a separator downstream from said expander for receiving a liquid-gas stream from expansion with said expander;

separating the liquid-gas stream with said separator into an upper gas stream and a lower liquid stream;

removing the liquid stream from said separator;

returning said liquid stream from said separator to said absorber which is positioned upstream from said separator and injecting it into an upper region of said absorber, said liquid stream being passed downwardly in said absorber for absorbing propane and heavier hydrocarbon compounds in said absorber;

removing the upper gas stream from said separator for compression into a residue gas;

delivering the bottom liquid stream from said absorber to distilling means located downstream from said separator for generating a bottom propane rich liquid product stream and an upper methane and ethane gas stream; and removing the bottom propane rich liquid product stream from said distilling means.

2. In the propane recovery process as set forth in claim 1, the method further comprising the step of cross-exchanging said liquid stream from said separator with the upper methane and ethane gas stream removed from said distilling means in a heat exchanger prior to returning said liquid stream to said absorber.

3. In the propane recovery process as set forth in claim 2, the method further comprising the step of cross-exchanging the upper gas stream from said separator with said natural gas stream prior to delivery of said natural gas stream to said absorber.

4. In the propane recovery process as set forth in claim 3, the method further comprising the step of combining said upper methane and ethane gas stream from said distilling means with a separate methane-rich gas stream from said absorber and injecting said combined streams into said separator for subsequent separation into the liquid stream and the upper gas stream.

5. In the propane recovery process as set forth in claim 4, the method further comprising the step of expanding said separate methane-rich gas stream from said absorber prior to combining same with said gas stream from said distillation column.

6. In a propane recovery system, an apparatus comprising:
an absorber for receiving a natural feed gas stream, said absorber providing a downwardly flowing liquid stream for absorbing propane and heavier hydrocarbon compounds therein, said absorber passing the natural feed gas stream upwardly in a counter current manner for providing an upper methane and ethane gas stream;

expansion means positioned downstream from said absorber, said expansion means receiving the upper methane and ethane gas stream for expanding the upper methane and ethane gas stream to produce a liquid-gas stream;

means for separating situated downstream from said expansion means, said separating means receiving the liquid-gas stream therefrom and dividing the liquid-gas stream into an upper gas stream and a lower liquid stream, said absorber receiving the lower liquid stream in an upper region thereof;

compression means located downstream from said separating means, said compression means receiving the upper gas stream from said separating means for compressing the upper gas stream into a residue gas; and distilling means located downstream from said absorber and receiving a bottom liquids stream therefrom, said distilling means providing a bottom propane product stream and an upper methane and ethane gas stream.

7. In the propane recovery system as set forth in claim 6, wherein said separating means comprises a separator.

8. In the propane recovery system as set forth in claim 7, wherein said distilling means comprises a deethanizer.

9. In the propane recovery system as set forth in claim 8, wherein the upper methane and ethane gas stream from said deethanizer is injected into said separator.

10. In the propane recovery system as set forth in claim 6, wherein said expansion means comprises a turbo-expander.

11. In the propane recovery system as set forth in claim 6, wherein said absorber comprises a reboiled absorber having a plurality of equilibrium absorption stages therein.

12. In the propane recovery system as set forth in claim 11, wherein said separating means comprises a reflux separator.

13. In the propane recovery system as set forth in claim 12, the apparatus further comprising a second reflux separator positioned downstream from said distilling means, said second reflux separator receiving the upper methane and ethane gas stream from said distilling means for generating an upper gas stream and a lower liquid stream, the lower liquid stream being returned to an upper region of said distilling means, the upper gas stream being combined with the upper gas stream from said first reflux separator for producing a residue gas.

14. In the propane recovery system as set forth in claim 13, the apparatus further comprising at least one heat exchanger for cooling the natural feed gas stream and warming the upper gas stream from said first reflux separator.

15. In the propane recovery system as set forth in claim 14, the apparatus further comprising a second heat exchanger receiving the combined upper gas streams from the first and second reflux separators for cooling the natural feed gas stream.

16. In the propane recovery system as set forth in claim 15, the apparatus further comprising a first and a second dividing means, said first dividing means dividing the natural gas feed stream into an upper and lower natural gas feed stream prior to cooling, said second dividing means dividing the upper natural gas feed stream into three streams prior to cooling and introducing the feed streams into said absorber.

17. In a propane recovery system, an apparatus comprising:

a first absorber for receiving a natural feed gas stream on a plurality of absorption stages, said absorber providing a downwardly flowing liquid stream for absorbing propane and heavier hydrocarbon compounds therein, said absorber passing the natural gas feed stream upwardly in a counter current manner for providing an upper methane and ethane gas stream;

expansion means positioned downstream from said first absorber, said expansion means receiving the upper methane and ethane gas stream to produce a liquid-gas stream;

a second absorber situated downstream from said expansion means, said second absorber receiving the liquid/gas stream therefrom and dividing the liquid/gas stream into an upper gas stream and a lower liquid stream, said first absorber receiving the lower liquid stream in an upper region thereof;

compression means located downstream from said second absorber, said compression means receiving the upper gas stream from said second absorber for compressing the upper gas stream into a residue gas stream; and distilling means located downstream from said first absorber and receiving a bottom liquids stream therefrom, said distilling means providing a bottom propane product stream and an upper methane and ethane gas stream.

18. In the propane recovery system as set forth in claim 17, the apparatus further comprising a reflux separator positioned downstream from said distilling means, said reflux separator receiving the upper methane and ethane gas stream from said distilling means for generating an upper gas stream and a lower liquid stream, the lower liquid stream being returned to an upper region of said distilling means, the upper gas stream being provided to an upper region of said second absorber.

19. In the propane recovery system as set forth in claim 18, the apparatus further comprising a heat exchanger positioned downstream from said reflux separator for cooling the upper gas stream, said heat exchanger receiving the lower liquid stream from said second absorber and using the lower liquid stream for cooling the upper gas stream.

20. In the propane recovery system as set forth in claim 19, wherein said distilling means comprises a deethanizer.

21. In the propane recovery system as set forth in claim 6, wherein said absorber comprises a separator.

22. In the propane recovery system as set forth in claim 21, wherein recycled liquids combine with said natural gas feed stream prior to the delivery of said natural gas feed stream to said separator.

* * * * *